(12) United States Patent
Mizushima et al.

(10) Patent No.: US 10,155,755 B2
(45) Date of Patent: Dec. 18, 2018

(54) QUINUCLIDINE DERIVATIVE

(71) Applicant: LTT BIO-PHARMA CO., LTD., Minato-ku (JP)

(72) Inventors: Tohru Mizushima, Minato-ku (JP); Yasunobu Yamashita, Minato-ku (JP); Naoki Yamakawa, Okayama (JP)

(73) Assignee: LTT BIO-PHARMA CO., LTD., Minato-ku (JP)

( * ) Notice: Subject to any disclaimer, the term of this patent is extended or adjusted under 35 U.S.C. 154(b) by 0 days.

(21) Appl. No.: 15/552,623

(22) PCT Filed: Feb. 25, 2016

(86) PCT No.: PCT/JP2016/055637
§ 371 (c)(1),
(2) Date: Aug. 22, 2017

(87) PCT Pub. No.: WO2016/140136
PCT Pub. Date: Sep. 9, 2016

(65) Prior Publication Data
US 2018/0051018 A1 Feb. 22, 2018

(30) Foreign Application Priority Data
Mar. 2, 2015 (JP) .................. 2015-040321

(51) Int. Cl.
*C07D 453/02* (2006.01)
*A61K 31/439* (2006.01)

(52) U.S. Cl.
CPC .......... *C07D 453/02* (2013.01); *A61K 31/439* (2013.01)

(58) Field of Classification Search
CPC ... C07D 453/00; C07D 453/02; A61K 31/439
See application file for complete search history.

(56) References Cited

U.S. PATENT DOCUMENTS

| | | | |
|---|---|---|---|
| 2003/0055080 A1 | 3/2003 | Fernandez Forner et al. | |
| 2006/0052427 A1 | 3/2006 | Rovati et al. | |
| 2009/0202514 A1 | 8/2009 | Yoneyama et al. | |
| 2016/0244439 A1 | 8/2016 | Wang et al. | |

FOREIGN PATENT DOCUMENTS

| | | |
|---|---|---|
| JP | 2003-504368 A | 2/2003 |
| JP | 2006-56890 A | 3/2006 |
| JP | 2008-189667 A | 8/2008 |
| WO | 01/04118 A2 | 1/2001 |
| WO | 2015/007073 A1 | 1/2015 |

OTHER PUBLICATIONS

International Search Report dated Apr. 26, 2016 in PCT/JP2016/055637 filed Feb. 25, 2016.
Dramane I. Lainé et al., "Discovery of Novel 1-Azoniabicyclo[2.2.2]octane Muscarinic Acetylcholine Receptor Antagonists", Journal of Medicinal Chemistry, 2009, vol. 52, No. 8, pp. 2493-2505.

*Primary Examiner* — Rebecca L Anderson
*Assistant Examiner* — Karen Cheng
(74) *Attorney, Agent, or Firm* — Oblon, McClelland, Maier & Neustadt, L.L.P.

(57) ABSTRACT

Provided are a quinuclidine derivative of formula (1) and a medicament comprising the quinuclidine derivative:

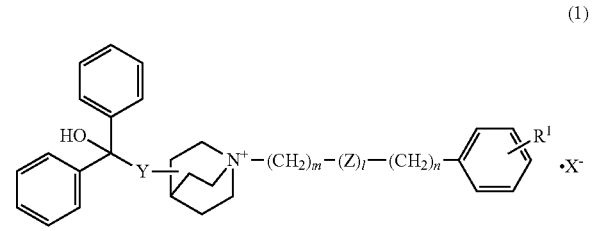

(1)

wherein $R^1$ represents a hydrogen atom, a halogen atom, a lower alkyl group, a haloalkyl group, a lower alkoxy group, or a haloalkoxy group; Y represents —C(C=O)—O—, or —CH$_2$O—; m represents an integer of 1 to 5; Z represents an oxygen atom or a sulfur atom; l represents a number of 0 or 1; n represents an integer of 0 to 4; $X^-$ represents an anion; and a substituent of a quinuclidine ring represents a 1,3-bond, or 1,4-bond, provided that when m is 3, l is 1, and n is 0, $R^1$ represents a halogen atom, a lower alkyl group, a haloalkyl group, a lower alkoxy group, or a haloalkoxy group.

19 Claims, 4 Drawing Sheets

QUINUCLIDINE DERIVATIVE

TECHNICAL FIELD

The present invention relates to a quinuclidine derivative, and to a medicament containing the quinuclidine derivative.

BACKGROUND ART

Chronic obstructive pulmonary disease (COPD) is a generic term for diseases that have been conventionally called chronic bronchitis or emphysema. COPD is a chronic disease of the lungs, which is caused by long-term inhalation exposure of harmful substances mainly containing tobacco smoke, and is said to be a lifestyle-related disease that occurs in middle-aged or older people against the background of smoking habit.

In the drug therapy for COPD, a bronchodilator (an anticholinergic drug, a $\beta_2$-agonist, or a theophylline drug) is mainly used, and an inhaled anticholinergic drug or an inhaled $\beta_2$-agonist that mainly dilates the bronchi for a long time is used. In addition, an inhaled corticosteroid is used in severe cases.

In recent years, as a drug effective for the treatment of COPD, for example, a quinuclidine derivative as a muscarinic $M_3$ receptor antagonist (Patent Literature 1), N-phenylbenzamide having a bronchodilation effect (Patent Literature 2), and a substance that inhibits the production or accumulation of chondroitin sulfate proteoglycans as an emphysema inhibitor (Patent Literature 3), have been reported.

CITATION LIST

Patent Literature

Patent Literature 1: WO 2001/004118
Patent Literature 2: JP 2006-56890 A
Patent Literature 3: JP 2008-189667 A

SUMMARY OF INVENTION

Technical Problem

However, although the quinuclidine derivative and the N-phenylbenzamide have some degree of the long-term bronchodilation effect, it cannot be said at present that they have a sufficient therapeutic effect on COPD.

Accordingly, an object of the present invention is to provide a novel compound having an excellent therapeutic effect on COPD.

Solution to Problem

Therefore, the present inventors have studied to develop a novel therapeutic drug for COPD, and have extensively studied based on the findings that a drug having only the long-term bronchodilation effect is not sufficient as the therapeutic drug for COPD, and a drug having a suppressive effect on chronic inflammation of the lungs together with the long-term bronchodilation effect is useful for COPD. As a result, the present inventors have found that a compound represented by the following general formula (1) has a long-term bronchodilation effect lasting longer than that of the compound described in Patent Literature 1, and further suppresses inflammation of the lungs, therefore, is particularly useful as a therapeutic drug for COPD; and thus have completed the present invention.

That is, the present invention provides the following [1] to [12].

[1] A quinuclidine derivative of the general formula (1),

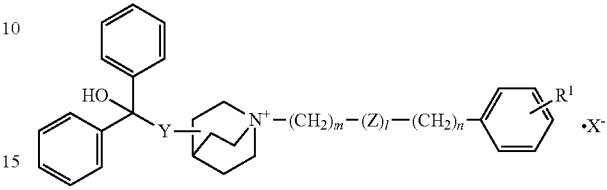

(1)

wherein $R^1$ represents a hydrogen atom, a halogen atom, a lower alkyl group, a haloalkyl group, a lower alkoxy group, or a haloalkoxy group; Y represents —C(=O)—O—, —CH$_2$—, or —CH$_2$O—; m represents an integer of 1 to 5; Z represents an oxygen atom or a sulfur atom; l represents a number of 0 or 1; n represents an integer of 0 to 4; $X^-$ represents an anion; and a substituent of the quinuclidine ring represents a 1,3-bond, or 1,4-bond, provided that when m is 3, l is 1, and n is 0, $R^1$ represents a halogen atom, a lower alkyl group, a haloalkyl group, a lower alkoxy group, or a haloalkoxy group.

[2] The quinuclidine derivative according to [1], wherein m is an integer of 2 to 5, l is a number of 0 or 1, and n is a number of 0 or 1.

[3] The quinuclidine derivative according to [1] or [2], wherein m is an integer of 2 to 5, l is 0 or 1, and n is 0.

[4] The quinuclidine derivative according to any one of [1] to [3], wherein m is 3, and l and n are 0.

[5] The quinuclidine derivative according to any one of [1] to [4], wherein the quinuclidine derivative is an (R) isomer.

[6] A medicament, comprising the quinuclidine derivative according to any one of [1] to [5] as an active ingredient.

[7] The medicament according to [6], wherein the medicament is a therapeutic agent for chronic obstructive pulmonary disease.

[8] A pharmaceutical composition, comprising the quinuclidine derivative according to any one of [1] to [5], and a pharmaceutically acceptable carrier.

[9] Use of the quinuclidine derivative according to any one of [1] to [5] for producing a medicament.

[10] The use according to [9], wherein the medicament is a therapeutic agent for chronic obstructive pulmonary disease.

[11] The quinuclidine derivative according to any one of [1] to [5], wherein the quinuclidine derivative is used for treating chronic obstructive pulmonary disease.

[12] A method for treating chronic obstructive pulmonary disease, comprising administering an effective amount of the quinuclidine derivative according to any one of [1] to [5].

Advantageous Effects of Invention

The quinuclidine derivative (1) of the present invention has a long-term bronchodilation effect lasting longer than before, further suppresses inflammation of the lungs, therefore, is useful as a therapeutic drug for COPD, and is particularly useful for the treatment of COPD with the inflammation such as chronic bronchitis.

DESCRIPTION OF EMBODIMENTS

Figure 1:
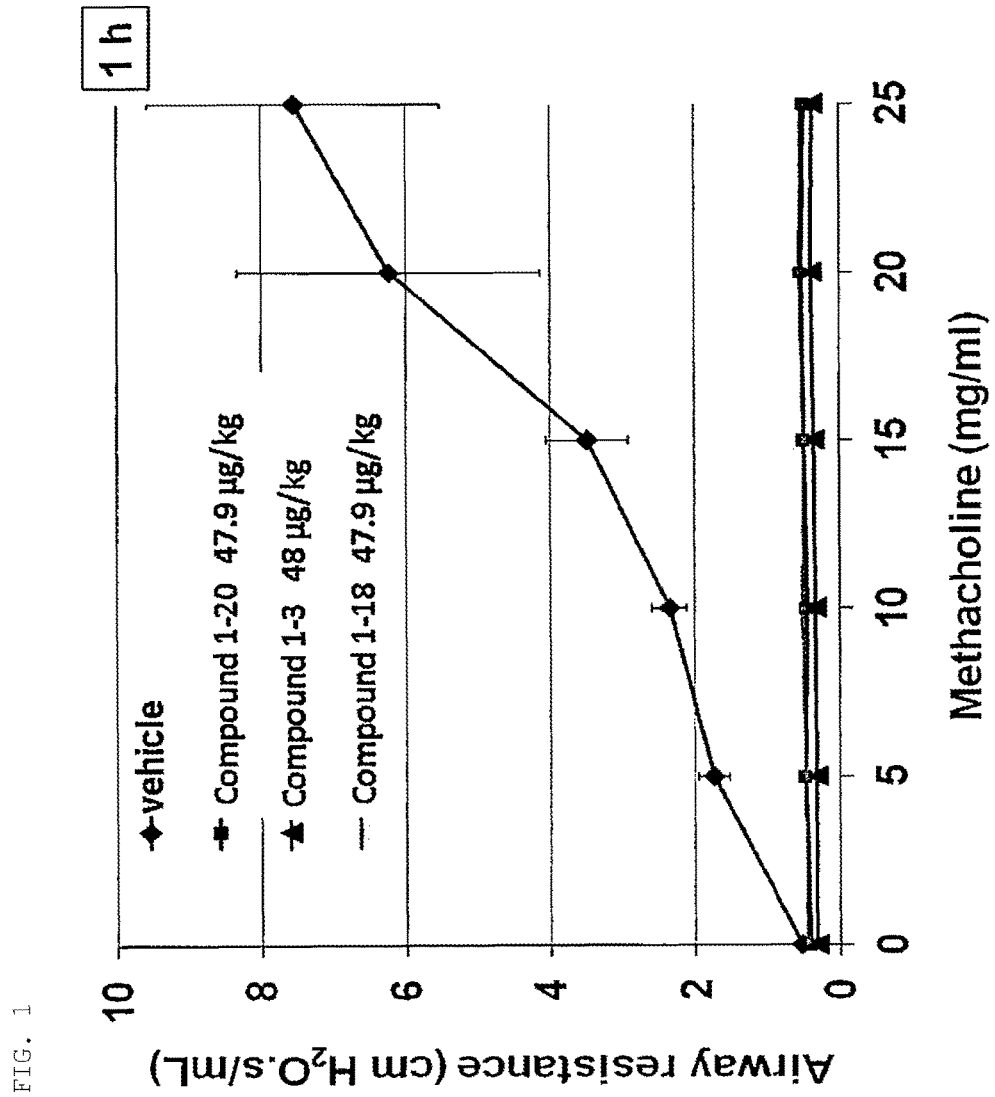
FIG. 1 shows effects of the compounds of the present invention on methacholine-induced airway constriction (1 hour after administration).

The quinuclidine derivative of the present invention is of the following general formula (1).

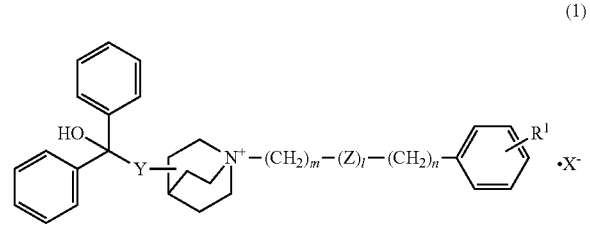

(1)

(In the formula, $R^1$ represents a hydrogen atom, a halogen atom, a lower alkyl group, a haloalkyl group, a lower alkoxy group, or a haloalkoxy group; Y represents —C(=O)—O—, —CH$_2$—, or —CH$_2$O—; m represents an integer of 1 to 5; Z represents an oxygen atom or a sulfur atom; l represents a number of 0 or 1; n represents an integer of 0 to 4; $X^-$ represents an anion; and a substituent of a quinuclidine ring represents a 1,3-bond, or 1,4-bond. Provided that when m is 3, l is 1, and n is 0, $R^1$ represents a halogen atom, a lower alkyl group, a haloalkyl group, a lower alkoxy group, or a haloalkoxy group.)

In general formula (1), Y represents —C(=O)—O—, —CH$_2$—, or —CH$_2$O—, and more preferably —C(=O)—O—.

Z represents an oxygen atom or a sulfur atom, and more preferably an oxygen atom.

Examples of the halogen atom represented by $R^1$ include a fluorine atom, a chlorine atom, a bromine atom, and an iodine atom. Examples of the lower alkyl group include a linear or branched chain alkyl group having 1 to 6 carbon atoms, and specific examples of the lower alkyl group include a methyl group, an ethyl group, an n-propyl group, an isopropyl group, an n-butyl group, an isobutyl group, a sec-butyl group, a tert-butyl group, an n-pentyl group, and an n-hexyl group. Among them, a methyl group and an ethyl group are more preferred, and a methyl group is particularly preferred. Examples of the haloalkyl group include a linear or branched chain alkyl group having 1 to 6 carbon atoms substituted with 1 to 3 halogen atoms, and specifically include a chloromethyl group, a trifluoromethyl group, and a trichloromethyl group.

Examples of the lower alkoxy group represented by $R^1$ include a linear or branched chain alkoxy group having 1 to 6 carbon atoms, and specifically include a methoxy group, an ethoxy group, an n-propyloxy group, an isopropyloxy group, an n-butyloxy group, an isobutyloxy group, a sec-butyloxy group, a tert-butyloxy group, an n-pentyloxy group, and an n-hexyloxy group. Among them, a methoxy group and an ethoxy group are more preferred, and a methoxy group is particularly preferred. Examples of the haloalkoxy group include a linear or branched chain alkoxy group having 1 to 6 carbon atoms substituted with 1 to 3 halogen atoms, and specifically include a trifluoromethoxy group, and a trichloromethoxy group.

$R^1$ is preferably a hydrogen atom, a halogen atom, a $C_1$-$C_6$ alkyl group, a halo-$C_1$-$C_6$ alkyl group, a $C_1$-$C_6$ alkoxy group, or a halo-$C_1$-$C_6$ alkoxy group.

The substitution position of $R^1$ is not particularly limited, and examples of the substitution position include an ortho position, a meta position, and a para position. Among them, an ortho position, or a para position is preferred, and particularly a para position is more preferred.

m represents an integer of 1 to 5, preferably an integer of 2 to 5, more preferably an integer of 2 to 4, and particularly preferably 3. l represents a number of 0 or 1. n represents an integer of 0 to 4, more preferably an integer of 0 to 2, and furthermore preferably 0 or 1.

It is preferred that m is an integer of 2 to 5, l is 0 or 1, and n is 0 or 1; more preferred that m is an integer of 2 to 5, l is 0 or 1, and n is 0; and furthermore preferred that m is 3, and l and n are 0.

$X^-$ represents an anion, and examples of the $X^-$ include a halogen anion, a trifluoroacetic acid anion, a sulfuric acid anion, a nitric acid anion, an acetic acid anion, an oxalic acid anion, and a succinic acid anion, and among them a halogen anion, and a trifluoroacetic acid anion are more preferred.

The bonding position of the substituent of a quinuclidine ring is 1,3-bond or 1,4-bond, and 1,3-bond is more preferred.

Preferred embodiments of the quinuclidine derivative (1) of the present invention are:

(1) Y is —C(=O)—O—, Z is an oxygen atom, $R^1$ is a hydrogen atom, a halogen atom, a $C_1$-$C_6$ alkyl group, a halo-$C_1$-$C_6$ alkyl group, a $C_1$-$C_6$ alkoxy group, or a halo-$C_1$-$C_6$ alkoxy group, m is an integer of 2 to 5, l is 0 or 1, n is 0 or 1, and $X^-$ is a halogen ion (provided that when $R^1$ is a hydrogen atom, not satisfy m=3, l=1, and n=0);

(2) Y is —C(=O)—O—, Z is an oxygen atom, $R^1$ is a hydrogen atom, a halogen atom, a $C_1$-$C_6$ alkyl group, a halo-$C_1$-$C_6$ alkyl group, a $C_1$-$C_6$ alkoxy group, or a halo-$C_1$-$C_6$ alkoxy group, m is an integer of 2 to 5, l is 0 or 1, n is 0, $X^-$ is a halogen ion (provided that when $R^1$ is a hydrogen atom, not satisfy m=3, l=1, and n=0);

(3) Y is —C(=O)—O—, Z is an oxygen atom, $R^1$ is a hydrogen atom, a halogen atom, a $C_1$-$C_6$ alkyl group, a halo-$C_1$-$C_6$ alkyl group, a $C_1$-$C_6$ alkoxy group, or a halo-$C_1$-$C_6$ alkoxy group, m is an integer of 2 to 5, l and n are 0, and $X^-$ is a halogen ion; or (4) Y is —C(=O)—O—, Z is an oxygen atom, $R^1$ is a hydrogen atom, m is an integer of 2 to 5, l and n are 0, and $X^{31}$ is a halogen ion.

In the quinuclidine derivative (1) of the present invention, since the carbon atom at position 3 of the quinuclidine skeleton is an asymmetric carbon atom, optical isomers exist. As the optical isomers, both an optically active isomer and a racemic isomer are included, and an (R) isomer is particularly preferred.

The quinuclidine derivative (1) of the present invention can be produced, for example, in accordance with the following reaction scheme.

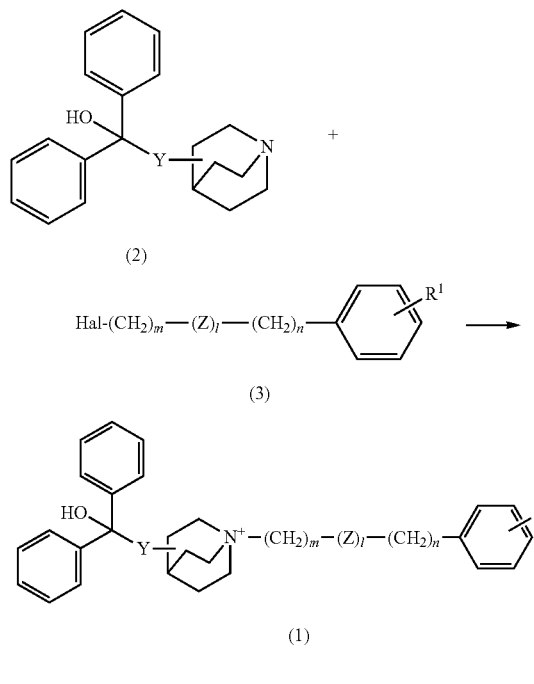

(In the formulae, Hal represents a halogen atom, Y, Z, $R^1$, l, m, and n are as defined above)

That is, the quinuclidine derivative (1) can be produced by reacting a compound (2) with a compound (3).

The reaction of the compound (2) with the compound (3) easily proceeds by heating to a temperature approximately room temperature to 100° C. As the reaction solvent, for example, dioxane, or acetonitrile can be used. Further, as the halogen atom (Hal) of the compound (2), for example, a bromine atom, or a chlorine atom is used.

The starting material compound (2) (the following compounds (2-a), (2-b), and (2-c)) can be produced, for example, in accordance with the following reaction schemes.

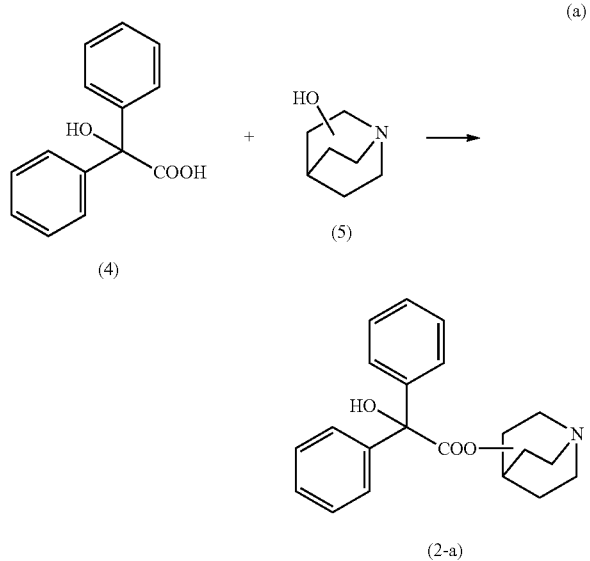

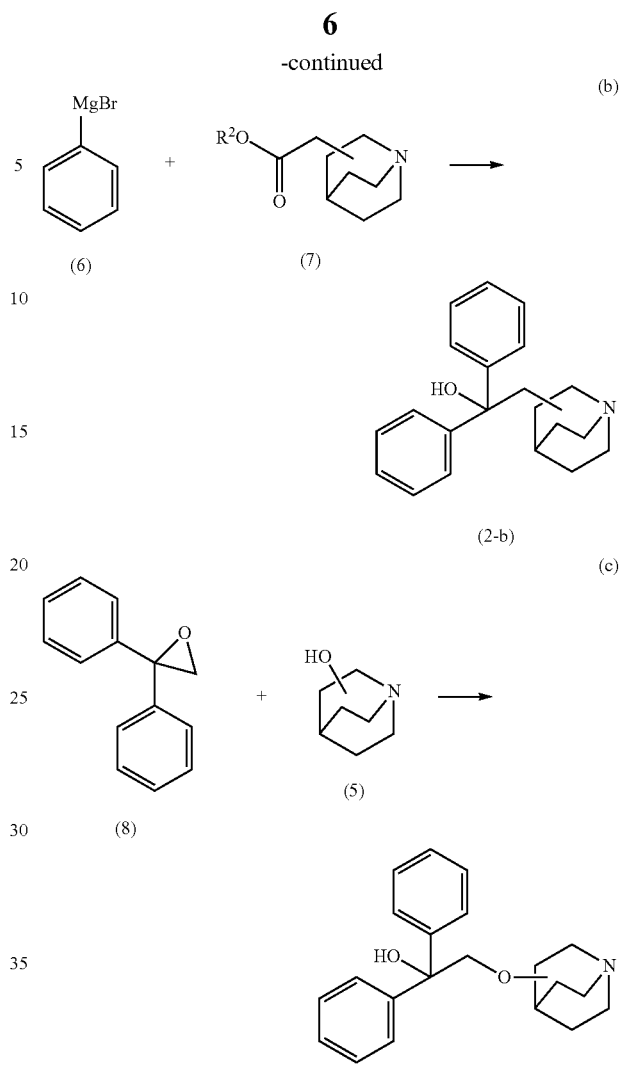

(In the formulae, $R^2$ represents an alkyl group)

That is, a compound (2-a) can be obtained by condensing benzylic acid (4) and quinuclidinol (5). The reaction of the benzylic acid (4) and the quinuclidinol (5) is preferably performed in the presence of a condensing agent such as carbonyldiimidazole (CDI). The reaction is preferably performed in the presence of a polar organic solvent such as dimethylformamide, or diethylformamide. The reaction is preferably performed at a temperature of from room temperature to the boiling point of the solvent for 1 to 24 hours while stirring the mixture.

By reacting a compound (6) with a compound (7), a compound (2-b) can be obtained. The reaction of the compound (6) with the compound (7) is a Grignard reaction, and for example, is preferably performed at a temperature of from room temperature to the boiling point of the solvent for 30 minutes to 24 hours in a solvent such as tetrahydrofuran while stirring the mixture.

By reacting a compound (8) with quinuclidinol (5), a compound (2-c) can be obtained. The reaction of the compound (8) and quinuclidinol (5) is, for example, preferably performed at a temperature of from room temperature to the boiling point of the solvent for 1 to 24 hours in a polar organic solvent such as dimethylformamide, or diethylformamide in the presence of a base such as sodium hydride while stirring the mixture.

The compound (2) may be used in the next reaction after being isolated or without being isolated. After completion of the reaction, the resultant product can be purified by extraction, solvent removal by distillation, or chromatography. Further, the purification of the object (1) of the present invention can also be performed in the similar manner.

In addition, in order to obtain the optically active isomer of the compound (1) of the present invention, (+) quinuclidinol, (−) quinuclidinol, (+) quinuclidine acetic acid ester, or (−) quinuclidine acetic acid ester may be used.

The quinuclidine derivative (1) of the present invention has a persistent and powerful bronchodilation effect, and further has an excellent anti-inflammatory effect, as shown in the Examples described later, therefore, is useful as a therapeutic agent for COPD with symptoms of emphysema and chronic bronchitis. In particular, the quinuclidine derivative (1) is useful as a therapeutic drug for COPD accompanied by inflammation.

Examples of the dosage form of the therapeutic agent for COPD of the compound (1) of the present invention include an inhalant, a transairway agent, nose drops, an injection, an oral agent (a tablet, granules, powders, and a capsule), ointment, cream, patch, and a suppository. Among them, an inhalant, a transairway agent, nose drops, and an oral agent are particularly preferred. In order to form the compound (1) into these forms of a pharmaceutical composition, the compound (1) can be formulated together with a pharmaceutically acceptable carrier. Examples of the carrier include water, ethanol, propylene glycol, polyethylene glycol, lactose, glucose, D-mannitol, starch, crystalline cellulose, calcium carbonate, kaolin, starch, gelatin, hydroxypropyl cellulose, hydroxypropyl methyl cellulose, polyvinyl pyrrolidone, ethanol, carboxymethyl cellulose, a carboxymethyl cellulose calcium salt, magnesium stearate, talc, acetyl cellulose, white soft sugar, titanium oxide, benzoic acid, paraoxybenzoic acid ester, sodium dehydroacetate, gum arabic, tragacanth, methylcellulose, egg yolk, surfactant, white soft sugar, simple syrup, citric acid, distilled water, ethanol, glycerin, propylene glycol, macrogol, sodium monohydrogen phosphate, sodium dihydrogen phosphate, sodium phosphate, glucose, sodium chloride, phenol, thimerosal, paraoxybenzoic acid ester, and sodium hydrogen sulfite.

The inhalant and the transairway agent mean a pharmaceutical composition for reaching the tissues of, for example, trachea, bronchi, and lungs, are suitably nose drops or a composition suitable for transnasal or transpulmonary administration, and are effective when administered with, for example, a nebulizer, an atomizer, a dropper, a pipette, or a cannula.

The compound (1) of the present invention can be effectively used by being administered in combination with, for example, a drug having an anticholinergic effect such as ipratropium, scopolamine, pirenzepine, tiotropium, oxitropium, aclidinium, glycopyrronium, or umeclidinium; or a β2-agonist such as indacaterol, vilanterol, salmeterol, or formoterol. Further, the compound (1) effectively exerts a therapeutic effect by using a steroid drug in combination.

In addition, the content of the active ingredient (quinuclidine derivative (1)) of the present invention in the pharmaceutical composition preparation of the present invention varies largely depending on the form of the preparation, and is not particularly limited, however, is usually 0.01 to 100% by mass, and preferably 1 to 100% by mass, based on the total amount of the composition.

The dose of the therapeutic agent for COPD of the present invention varies depending on the condition and age of the patient to be administered, and the administration method, and is preferably 1.0 μg to 10 mg per day for an adult as the quinuclidine derivative (1). In addition, this dose may also be administered in 1 to 4 divided doses per day, and is preferably once a day.

EXAMPLES

Hereinafter, the present invention will be described in more detail by way of Examples.

Test Example 1

Human $M_3$ Receptor Antagonist Activity

Measurement of the receptor binding ability was performed by using a transgenic human $M_3$ receptor expression CHO cell membrane, 1-[N-methyl-$^3$H] scopolamine methyl bromide ([$^3$H]NMS, specific activity of 82 Ci/mmol). Protein concentration of the cell membrane was 2 μg per well, concentration of the [$^3$H]NMS was 1.0 nM.

Range of the antagonist concentration ($10^{-4}$ to $10^{-11}$ M) was tested by creating a comparison curve. Unspecific binding was measured in the presence of 1 μM of atropine.

The reagent was adjusted to a total volume of 100 μL with a binding buffer (phosphate buffer/saline). The mixture was incubated at room temperature for 2 hours so as to reach equilibrium, and then the resultant mixture was transplanted to a GF/C filter plate that had been pretreated with a washing buffer containing 0.05% polyethyleneimine for 1 hour.

The bound [$^3$H]NMS and the free [$^3$H]NMS were separated by rapid vacuum filtration, and washed three times with a rinse buffer (50 mM of Tris, 100 mM of saline, and pH of 7.4). The obtained filter was dried, and then onto the dried filter, a solid scintillator, MeltiLex A (manufactured by PerkinElmer, Inc.) was fused, and the measurement and quantification were performed by using a β-counter (MicroBeta microplate scintillation counter (Trilux)).

The Ki value was calculated by the following equation. ([L]:[$^3$H]NMS concentration, Kd: dissociation constant of [$^3$H]NMS)

$$Ki=IC50/(1+[L]/Kd)$$

The Ki value (nM) of the obtained compound was shown in each Example.

Example 1

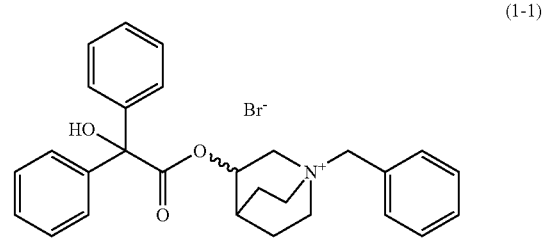 [SMILES: O=C(OC1C[N+]2(Cc3ccccc3)CCC1CC2)C(O)(c1ccccc1)c1ccccc1 ; [Br-]]

(1-1)

Into 15 mL of dimethylformamide (DMF), 1.5 g (6.57 mmol) of benzylic acid, 997 mg (7.85 mmol) of (±) quinuclidinol, and 1.59 g (9.85 mmol) of carbodiimidazole (CDI) were added, and a tertiary amine was obtained. Into 60 ml of dioxane, the obtained tertiary amine (1.6 g, 4.8 mmol), and benzyl bromide (1.08 g, 6.4 mmol) were added to give a compound (1-1) (2.24 g, yield 65%).

$^1$H NMR (DMSO-d$_6$): δ=7.26-7.33 (m, 10H), 7.47-7.55 (m, 5H), 6.76 (s, 1H), 5.21 (br, 1H), 4.47 (dd, J=13.1, 10.5 Hz, 2H), 3.40 (d, J=7.8 Hz, 1H), 3.86 (dd, J=11.2, 8.4 Hz, 1H), 3.32 (m, 2H), 3.25 (d, J=13.9 Hz, 1H), 3.01 (br, 1H), 2.22 (br, 1H), 1.51-1.93 (m, 4H)

mp 219.2-220.4° C.

Ki (M$_3$ receptor)=4.12 nM

Examples 2 to 41

Compounds of Examples 2 to 41 were obtained in the same manner as in Example 1. The Ki values for M$_3$ receptors of the obtained compounds were also shown.

Example 2

Compound (1-2)

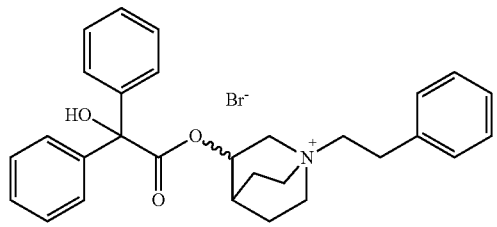

(1-2)

$^1$H NMR (DMSO-d$_6$): δ=7.24-7.41 (m, 15H), 6.79 (s, 1H), 5.26 (br, 1H), 3.91 (m, 1H), 3.35-3.60 (m, 6H), 2.89-3.14 (m, 3H), 2.28 (br, 1H), 1.53-1.99 (m, 4H)

mp 223.2-223.9° C.

Ki (M$_3$ receptor)=0.083 nM

Example 3

Compound (1-3)

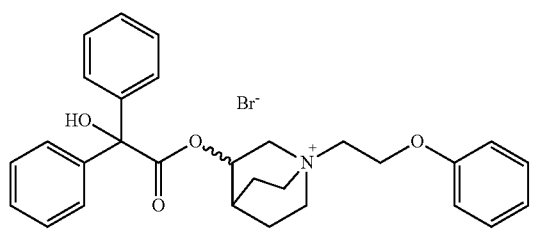

(1-3)

$^1$H NMR (DMSO-d$_6$): δ=6.94-7.52 (m, 15H), 6.75 (s, 1H), 5.20 (br, 1H), 4.37 (m, 2H), 4.01 (m, 1H), 3.15-3.66 (m, 6H), 3.12 (m, 1H), 2.24 (m, 1H), 1.50-1.94 (m, 4H)

mp 213.5-214.2° C.

Ki (M$_3$ receptor)=0.13 nM

Example 4

Compound (1-4)

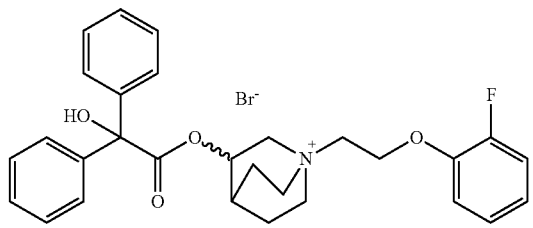

(1-4)

$^1$H NMR (DMSO-d$_6$): δ=7.01-7.38 (m, 14H), 6.77 (s, 1H), 5.23 (m, 1H), 4.05 (m, 1H), 3.74 (m, 2H), 3.20-3.41 (m, 6H), 3.14 (m, 1H), 2.27 (m, 1H), 1.91 (m, 2H), 1.52-1.70 (m, 2H)

mp 223.4-224.1° C.

Ki (M3 receptor)=0.114 nM

Example 5

Compound (1-5)

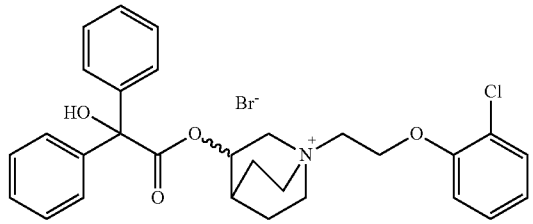

(1-5)

$^1$H NMR (DMSO-d$_6$): δ=7.02-7.48 (m, 14H), 6.95 (s, 1H), 5.24 (m, 1H), 4.02 (m, 1H), 3.89 (m, 2H), 3.21-3.42 (m, 6H), 3.24 (m, 1H), 2.20 (m, 1H), 1.45-1.90 (m, 4H)

mp 211.4-212.2° C.

Ki (M3 receptor)=2.39 nM

Example 6

Compound (1-6)

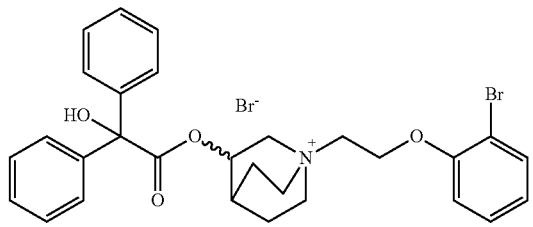

(1-6)

$^1$H NMR (DMSO-d$_6$): δ=6.95-7.62 (m, 14H), 6.89 (s, 1H), 5.22 (m, 1H), 4.04 (m, 1H), 3.78 (m, 2H), 3.40-3.60 (m, 6H), 3.21 (m, 1H), 2.22 (m, 1H), 1.55-1.98 (m, 4H)

mp 202.9-203.9° C.

Ki (M3 receptor)=0.458 nM

Example 7
Compound (1-7)
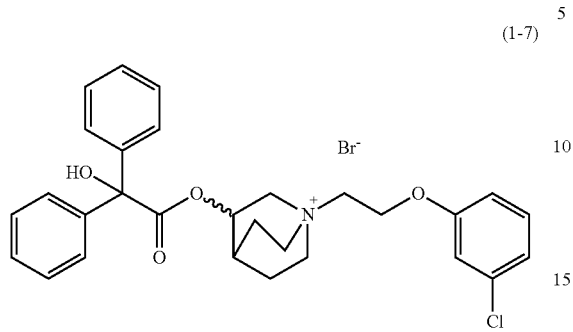
¹H NMR (DMSO-d₆): δ=6.95-7.36 (m, 14H), 6.75 (s, 1H), 5.20 (m, 1H), 4.41 (m, 2H), 4.04 (m, 1H), 3.40-3.68 (m, 6H), 3.14 (m, 1H), 2.24 (m, 1H), 1.49-1.92 (m, 4H).
mp 182-184° C.
Example 8
Compound (1-8)
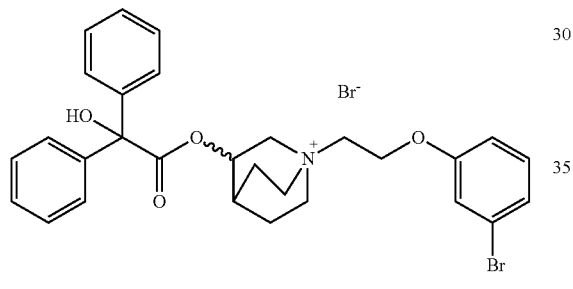
¹H NMR (DMSO-d₆): δ=6.91-7.36 (m, 14H), 6.75 (s, 1H), 5.20 (m, 1H), 4.42 (m, 2H), 4.04 (m, 1H), 3.40-3.69 (m, 6H), 3.12 (m, 1H), 2.24 (m, 1H), 1.49-1.96 (m, 4H).
mp 188-190° C.
Example 9
Compound (1-9)
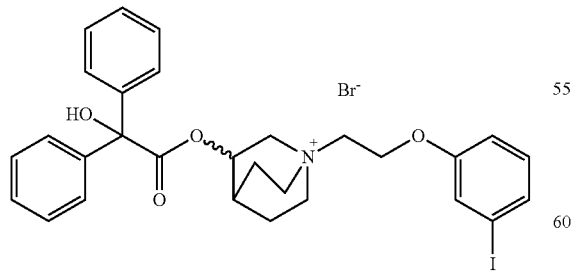
¹H NMR (DMSO-d₆): δ=6.95-7.36 (m, 14H), 6.75 (s, 1H), 5.20 (m, 1H), 4.40 (m, 2H), 4.03 (m, 1H), 3.39-3.67 (m, 6H), 3.11 (m, 1H), 2.24 (m, 1H), 1.49-1.96 (m, 4H).
mp 150-153° C.
Example 10
Compound (1-10)
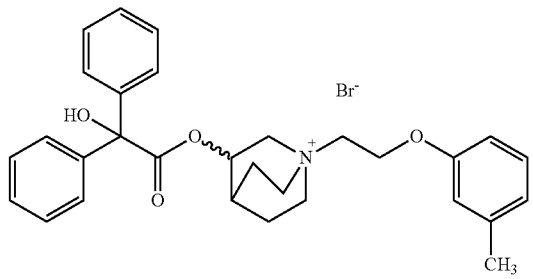
¹H NMR (DMSO-d₆): δ=6.80-7.25 (m, 14H), 6.77 (s, 1H), 5.20 (m, 1H), 4.35 (m, 2H), 4.04 (m, 1H), 3.39-3.67 (m, 6H), 3.13 (m, 1H), 2.25 (s, 3H), 2.24 (m, 1H), 1.49-1.99 (m, 4H).
mp 169-173° C.
Example 11
Compound (1-11)
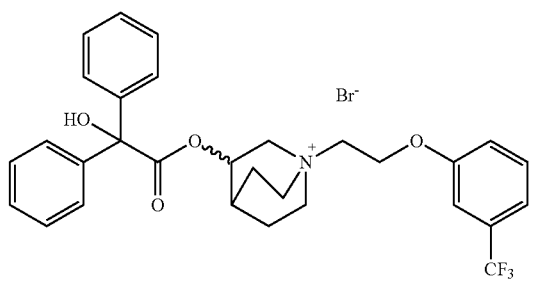
¹H NMR (DMSO-d₆): δ=7.22-7.55 (m, 14H), 6.75 (s, 1H), 5.21 (m, 1H), 4.48 (m, 2H), 4.04 (m, 1H), 3.41-3.71 (m, 6H), 3.14 (m, 1H), 2.25 (m, 1H), 1.50-1.83 (m, 4H).
mp 155-157° C.
Example 12
Compound (1-12)
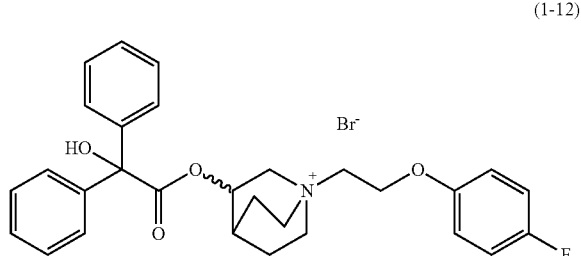

¹H NMR (DMSO-d₆): δ=7.12-7.35 (m, 14H), 6.76 (s, 1H), 5.20 (m, 1H), 4.36 (m, 2H), 4.00 (m, 1H), 3.46-3.70 (m, 6H), 3.16 (m, 1H), 2.24 (m, 1H), 1.48-1.83 (m, 4H).
mp 211-213° C.

Example 13

Compound (1-13)

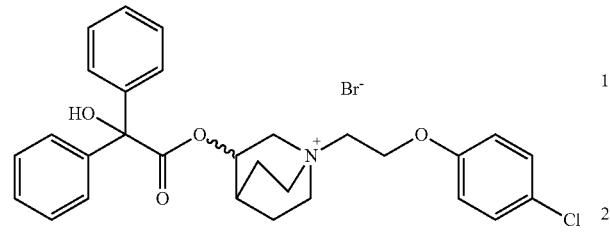

(1-13)

¹H NMR (DMSO-d₆): δ=6.95-7.37 (m, 14H), 6.76 (s, 1H), 5.20 (m, 1H), 4.38 (m, 2H), 4.04 (m, 1H), 3.40-3.71 (m, 6H), 3.16 (m, 1H), 2.23 (m, 1H), 1.48-1.87 (m, 4H).
mp 205-207° C.

Example 14

Compound (1-14)

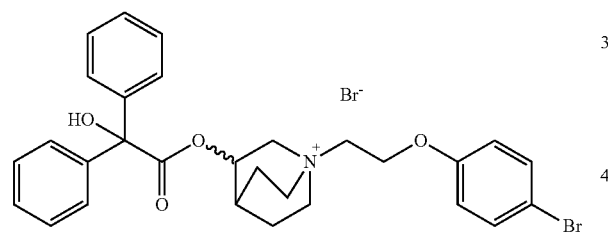

(1-14)

¹H NMR (DMSO-d₆): δ=7.47-7.47 (m, 2H), 7.24-7.36 (m, 10H), 6.91-6.93 (m, 2H), 6.75 (s, 1H), 5.20 (m, 1H), 4.38 (m, 2H), 3.98-4.04 (m, 1H), 3.67-3.68 (m, 2H), 3.40-3.54 (m, 4H), 3.11-3.17 (m, 1H), 2.24 (m, 1H), 1.82-1.96 (m, 2H), 1.64-1.70 (m, 1H), 1.48-1.52 (m, 1H).
mp 195-196° C.

Example 15

Compound (1-15)

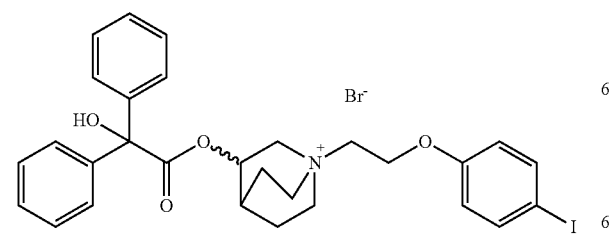

(1-15)

¹H NMR (DMSO-d₆): δ=7.61-7.63 (m, 2H), 7.24-7.35 (m, 10H), 6.78-6.80 (m, 2H), 6.75 (s, 1H), 5.20 (m, 1H), 4.37 (m, 2H), 3.98-4.03 (m, 1H), 3.66-3.67 (m, 2H), 3.39-3.53 (m, 4H), 3.10-3.16 (m, 1H), 2.24 (m, 1H), 1.82-1.96 (m, 2H), 1.64-1.70 (m, 1H), 1.48-1.52 (m, 1).
mp 185-188° C.

Example 16

Compound (1-16)

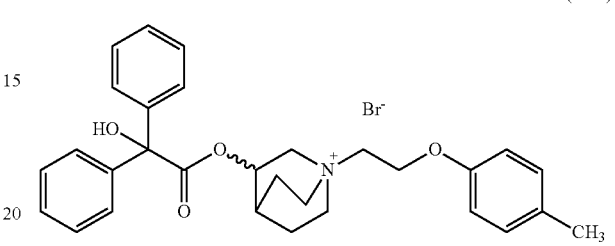

(1-16)

¹H NMR (DMSO-d₆): δ=7.24-7.36 (m, 10H), 7.09-7.10 (m, 2H), 6.82-6.84 (m, 2H), 6.77 (s, 1H), 5.20 (m, 1H), 4.33 (m, 2H), 3.99-4.03 (m, 1H), 3.61-3.70 (m, 2H), 3.42-3.54 (m, 4H), 3.11-3.16 (m, 1H), 2.21-2.24 (m, 4H), 1.84-1.95 (m, 2H), 1.64-1.70 (m, 1H), 1.47-1.52 (m, 1H).
mp 203-204° C.

Example 17

Compound (1-17)

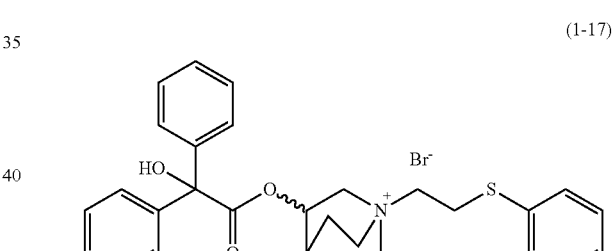

(1-17)

¹H NMR (DMSO-d₆): δ=7.22-7.39 (m, 15H), 6.75 (s, 1H), 5.19 (br, 1H), 3.89-3.93 (m, 1H), 3.34-3.49 (m, 8H), 3.04-3.09 (m, 1H), 2.23 (br, 1H), 1.80-1.94 (m, 2H), 1.60-1.66 (m, 1H), 1.45-1.49 (m, 1H).
mp 176-177° C.

Example 18

Compound (1-18)

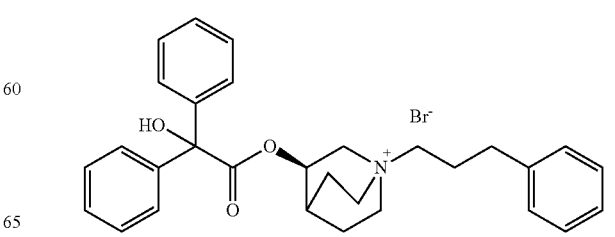

(1-18)

¹H NMR (DMOS-d₆): =7.19-7.39 (m, 15H), 6.75 (s, 1H), 5.20 (br, 1H), 3.93 (m, 1H), 3.33-3.40 (m, 2H), 3.14-3.22 (m, 4H), 2.99 (m, 1H), 2.56 (t, J=7.9 Hz, 2H), 2.25 (br, 1H), 1.52-1.97 (m, 6H)
mp 243.1-244.4° C.
Ki (M₃ receptor)=0.014 nM Example 19

Compound (1-19) (S) isomer (1-19)

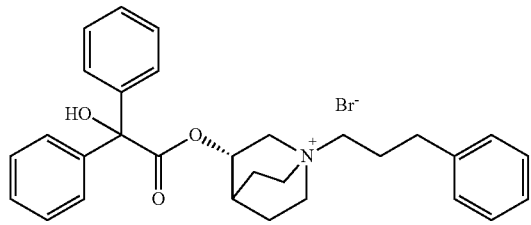

NMR is the same as in Example 18
mp 243.2-244.1° C.
Ki (M₃ receptor)=2.09 nM

Example 20

Compound (1-20)

(1-20)

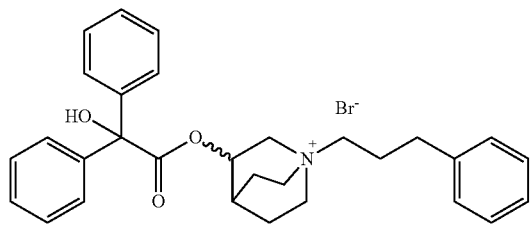

NMR is the same as in Example 18
mp 210.5-211.1° C.
Ki (M₃ receptor)=0.029 nM

Example 21

Compound (1-21)

(1-21)

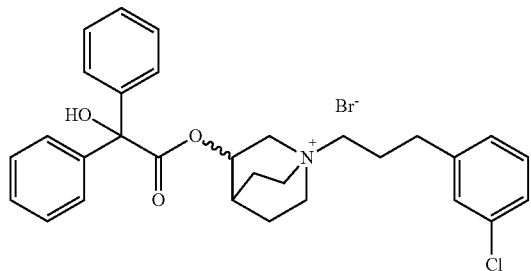

¹H NMR (DMSO-d₆): δ=7.20-7.36 (m, 14H), 6.76 (s, 1H), 5.18 (m, 1H), 3.86 (m, 1H), 3.22-3.39 (m, 6H), 3.00 (m, 1H), 2.56 (m, 2H), 1.47-2.22 (m, 7H).
mp 131-133° C.

Example 22

Compound (1-22)

(1-22)

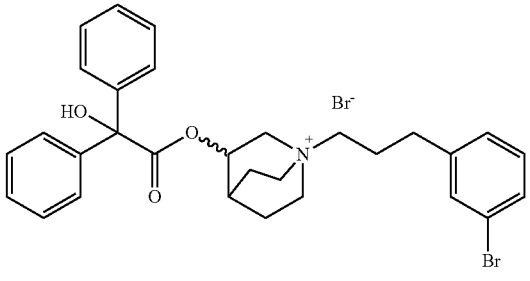

¹H NMR (DMSO-d₆): δ=7.23-7.48 (m, 14H), 6.74 (s, 1H), 5.18 (m, 1H), 3.86 (m, 1H), 3.14-3.52 (m, 6H), 2.94 (m, 1H), 2.53 (m, 2H), 1.48-2.23 (m, 7H).
mp 194-195° C.

Example 23

Compound (1-23)

(1-23)

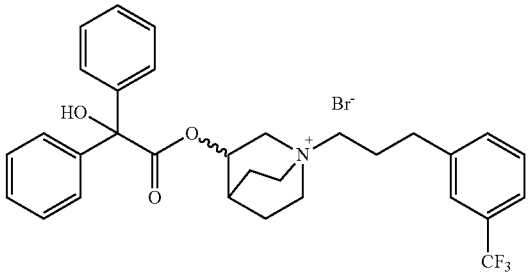

¹H NMR (DMOS-d₆) δ 7.23-7.63 (m, 14H), 6.76 (s, 1H), 5.19 (m, 1H), 3.85 (m, 1H), 3.23-3.40 (m, 6H), 2.96 (m, 1H), 2.64 (m, 2H), 1.48-2.23 (m, 7H).
mp 168-169° C.

Example 24

Compound (1-24)

(1-24)

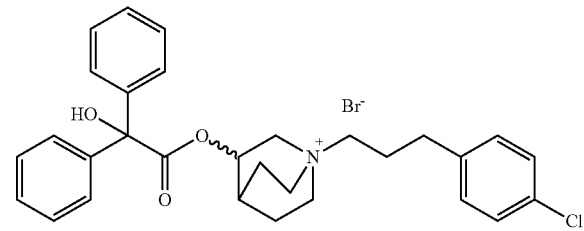

¹H NMR (DMSO-d₆): δ=7.24-7.29 (m, 14H), 6.73 (s, 1H), 5.17 (m, 1H), 3.83 (m, 1H), 3.21-3.38 (m, 6H), 3.05 (m, 1H), 2.53 (m, 2H), 1.47-2.22 (m, 7H)
mp 211.5-212.1° C.
Ki (M3 receptor)=0.31 nM

Example 25

Compound (1-25)

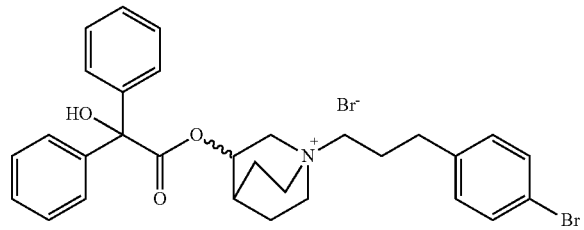
(1-25)

¹H NMR (DMSO-d₆): δ=7.18-7.48 (m, 14H), 6.74 (s, 1H), 5.17 (m, 1H), 3.83 (m, 1H), 3.11-3.37 (m, 6H), 3.01 (m, 1H), 2.53 (m, 2H), 1.48-2.22 (m, 7H)
mp 219.5-219.9° C.
Ki (M3 receptor)=1.26 nM

Example 26

Compound (1-26)

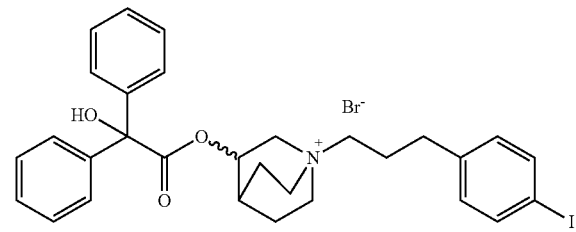
(1-26)

¹H NMR (DMSO-d₆): δ=7.04-7.65 (m, 14H), 6.75 (s, 1H), 5.18 (m, 1H), 3.85 (m, 1H), 3.10-3.38 (m, 6H), 2.98 (m, 1H), 2.51 (m, 2H), 2.21 (m, 1H), 1.48-1.90 (m, 6H).
mp 184-185° C.

Example 27

Compound (1-27)

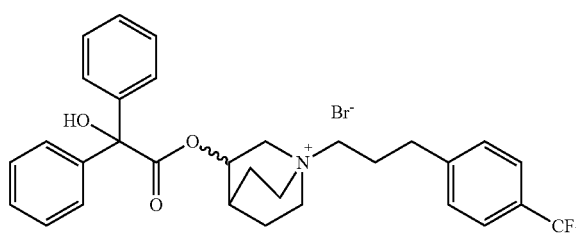
(1-27)

¹H NMR (DMSO-d₆): δ=7.36-7.66 (m, 14H), 6.75 (s, 1H), 5.18 (m, 1H), 3.85 (m, 1H), 3.14-3.39 (m, 6H), 3.14 (m, 1H), 2.63 (m, 2H), 1.49-2.42 (m, 7H).
mp 221.5-221.9° C.
Ki (M3 receptor)=0.67 nM

Example 28

Compound (1-28)

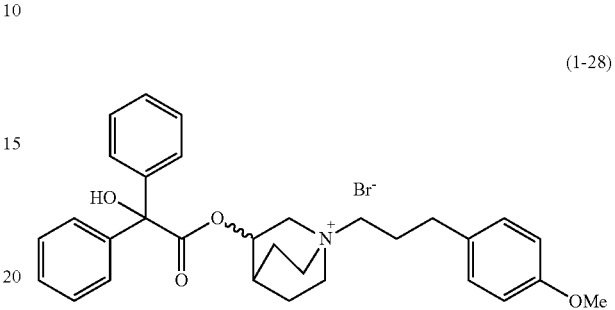
(1-28)

¹H NMR (DMOS-d₆): δ=6.82-7.40 (m, 15H), 5.21 (m, 1H), 3.85 (m, 1H), 3.70 (s, 3H), 3.10-3.40 (m, 6H), 2.98 (m, 1H), 2.51 (m, 2H), 1.48-2.22 (m, 7H)
mp 218.3-218.9° C.
Ki (M3 receptor)=1.29 nM

Example 29

Compound (1-29)

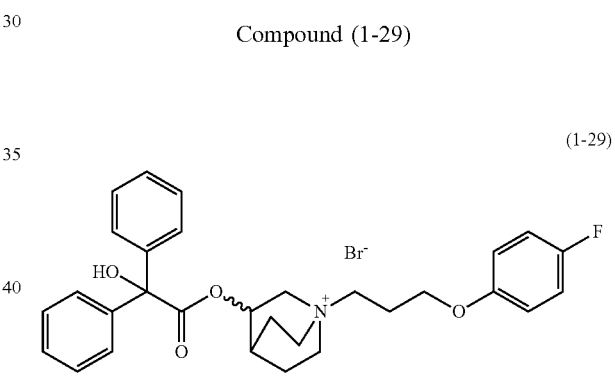
(1-29)

¹H NMR (DMOS-d₆): =6.92-7.38 (m, 14H), 6.77 (s, 1H), 5.20 (m, 1H), 3.91 (m, 3H), 3.27-3.44 (m, 6H), 3.06 (m, 1H), 1.47-2.11 (m, 7H)
mp 211.1-212.0° C.
Ki (M₃ receptor)=0.19 nM

Example 30

Compound (1-30)

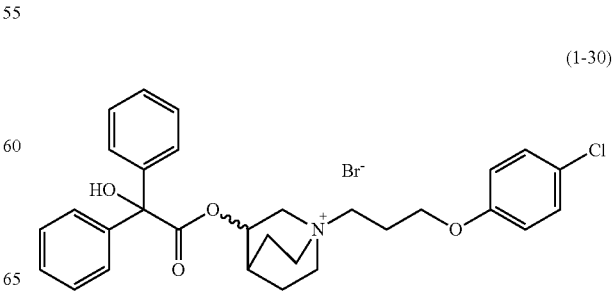
(1-30)

$^1$H NMR (DMOS-d$_6$): δ=6.93-7.38 (m, 14), 6.77 (s, 1H), 5.20 (m, 1H), 3.98-4.00 (m, 3H), 3.27-3.45 (m, 6H), 3.04 (m, 1H), 1.47-2.1 (m, 7H)
mp 208.8-210.0° C.
Ki (M$_3$ receptor)=0.084 nM Example 31

Compound (1-31)

$^1$H NMR (DMOS-d$_6$): δ=6.75-7.38 (m, 15H), 5.20 (br, 1H), 3.95 (m, 3H), 3.27-3.43 (m, 6H), 3.06 (m, 1H), 1.48-2.24 (m, 10H)
mp 218.1-219.3° C.
Ki (M$_3$ receptor)=0.058 nM Example 34

Compound (1-34)

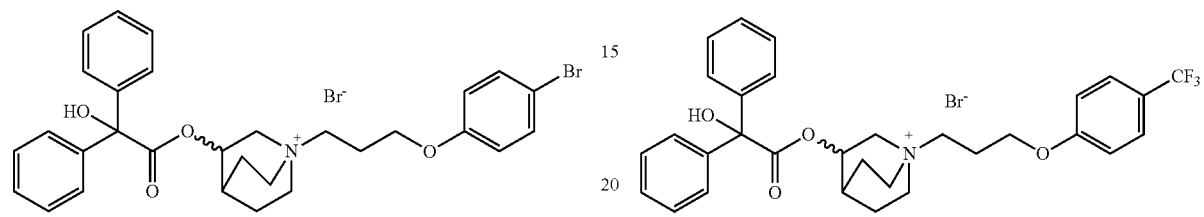

$^1$H NMR (DMOS-d$_6$): δ=6.75-7.44 (m, 15H), 5.19 (br, 1H), 3.87-3.98 (m, 3H), 3.27-3.43 (m, 5H), 3.01 (m, 1H), 1.49-2.46 (m, 8H)
mp 214.5-215.4° C.
Ki (M$_3$ receptor)=0.32 nM Example 32

Compound (1-32)

$^1$H NMR (DMOS-d$_6$): δ=7.10-7.65 (m, 14H), 6.74 (s, 1H), 5.21 (br, 1H), 4.09 (m, 2H), 3.93 (m, 1H), 3.28-3.45 (m, 6H), 3.03 (m, 1H), 1.49-2.25 (m, 7H)
mp 210.5-211.2° C.
Ki (M$_3$ receptor)=2.7 nM Example 35

Compound (1-35)

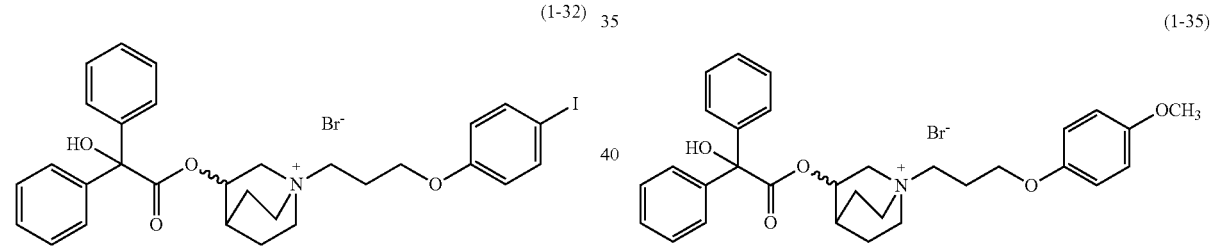

$^1$H NMR (DMOS-d$_6$): δ=7.26-7.58 (m, 14H), 6.75 (m, 3H), 5.19 (br, 1H), 3.90 (m, 3H), 3.27-3.41. (m, 6H), 3.04 (m, 1H), 1.47-2.24 (m, 7H)
mp 208.1-209.0° C.
Ki (M$_3$ receptor)=0.22 nM Example 33

Compound (1-33)

$^1$H NMR (DMOS-d$_6$): δ=6.75-7.38 (m, 15H), 5.20 (br, 1H), 3.90 (m, 3H), 3.66 (s, 3H), 3.27-3.44 (m, 6H), 3.05 (m, 1H), 1.49-2.24 (m, 10H)
mp 213.4-214.3° C.
Ki (M$_3$ receptor)=5.89 nM Example 36

Compound (1-36)

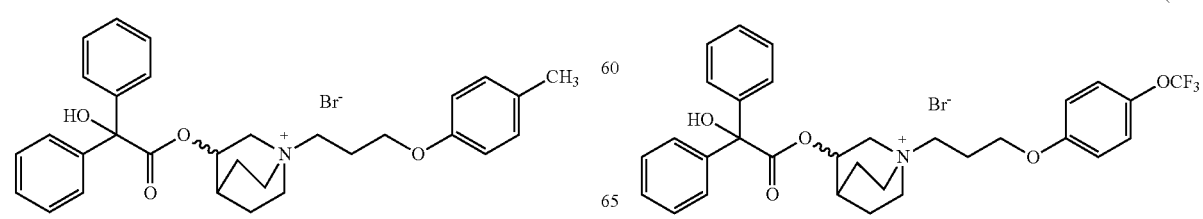

$^1$H NMR (DMOS-d$_6$): δ=7.01-7.38 (m, 14H), 6.76 (s, 1H), 5.20 (br, 1H), 4.02 (m, 3H), 3.36-3.45 (m, 6H), 3.06 (m, 1H), 1.48-2.24 (m, 7H)

mp 215.1-216.9° C.

Ki (M$_3$ receptor)=0.39 nM

Example 37

Compound (1-37)

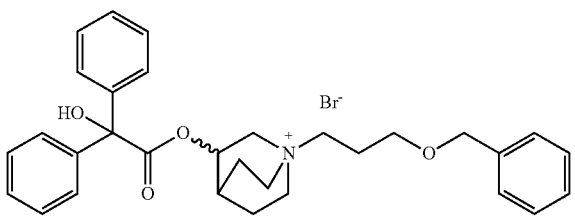

(1-37)

$^1$H NMR (DMOS-d$_6$): δ=7.27-7.40 (m, 15H), 6.76 (s, 1H), 5.21 (br, 1H), 4.46 (s, 2H), 3.85 (m, 1H), 3.46 (t, J=5.8 Hz, 2H), 3.21-3.39 (m, 6H), 3.03 (m, 1H), 2.25 (m, 1H), 1.49-1.95 (m, 6H)

mp 228.2-229.9° C.

Ki (M$_3$ receptor)=2.70 nM

Example 38

Compound (1-38)

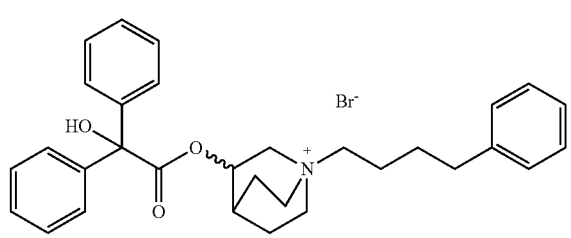

(1-38)

$^1$H NMR (DMOS-d$_6$): δ=7.19-7.39 (m, 15H), 6.76 (s, 1H), 5.20 (br, 1H), 3.80 (m, 1H), 3.31-3.40 (m, 3H), 3.18 (m, 3H), 2.95 (m, 1H), 2.60 (m, 2H), 2.25 (br, 1H), 1.55-1.91 (m, 8H)

mp 224.2-224.9° C.

Ki (M$_3$ receptor)=0.63 nM

Example 39

Compound (1-39)

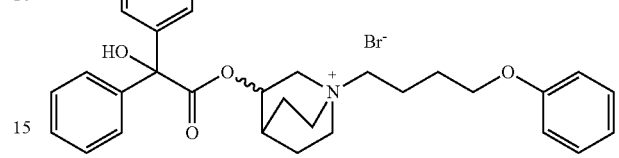

(1-39)

$^1$H NMR (DMOS-d$_6$): δ=6.91-7.40 (m, 15H), 6.77 (s, 1H), 5.20 (br, 1H), 3.99 (t, J=5.4 Hz, 2H), 3.86 (m, 1H), 3.19-3.41 (m, 6H), 3.01 (m, 1H), 2.26 (br, 1H), 1.49-1.98 (m, 8H)

mp 194.5-195.5° C.

Ki (M$_3$ receptor)=2.98 nM

Example 40

Compound (1-40)

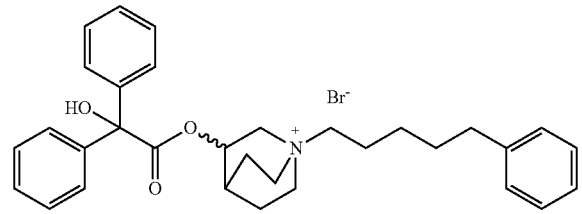

(1-40)

$^1$H NMR (DMOS-d$_6$): δ=7.15-7.40 (m, 15H), 6.77 (s, 1H), 5.23 (br, 1H), 3.82 (m, 1H), 3.26-3.34 (m, 3H), 3.10-3.22 (m, 3H), 2.96 (m, 1H), 2.58 (t, J=7.6 Hz, 2H), 2.25 (m, 1H), 1.21-1.98 (m, 10H)

mp 201.1-202.4° C.

Ki (M$_3$ receptor)=2.53 nM

Example 41

Compound (1-41)

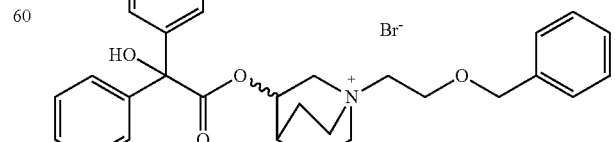

(1-41)

¹H NMR (DMOS-d₆): δ 7.27-7.48 (m, 15H), 6.77 (s, 1H), 5.20 (br, 1H), 4.49 (br, 1H), 3.96 (m, 1H), 3.80 (m, 3H), 3.37-3.63 (m, 7H), 3.22 (m, 1H), 2.26 (m, 1H), 53-1.95 (m, 3H)

mp 222.3?223.3° C.

Ki (M3 receptor)=0.12 nM

Example 42

Compound (1-42)

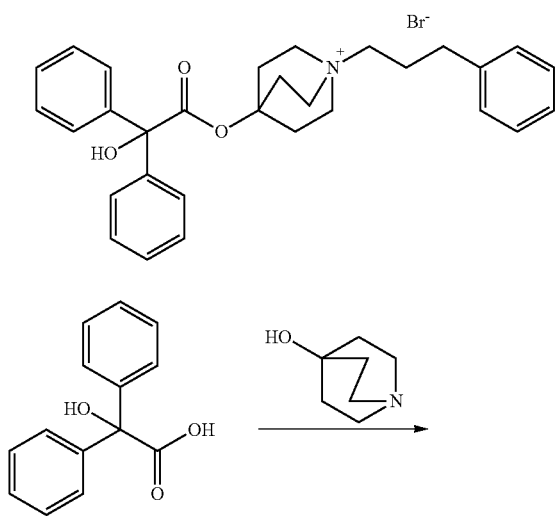

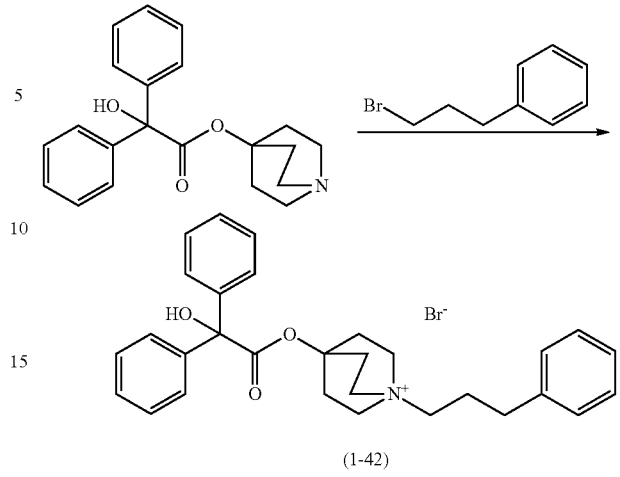

(2) Under an Ar atmosphere, 1.50 g of quinuclidinol benzilic acid ester and 30 mL of dry acetone were charged, and then 1.35 mL of 3-phenylpropyl bromide was added to the mixture at 20° C. to 30° C. The resultant mixture was stirred at the same temperature for 2 days (45 h).

The reaction mixture was ice-cold stirred for 4 hours, and then the precipitated crystals were collected by filtration, washed with 30 mL (20V)×3 of isopropyl ether (IPE), and dried at a bath temperature of 50° C. to 55° C. for 3 hours under reduced pressure, to give the target object (1.86 g) as white crystals.

¹H NMR (DMSO-d₆): δ=7.21-7.36 (m, 15H), 6.62 (s, 1H), 3.57-3.60 (m, 6H), 3.16-3.31 (m, 2H), 2.52-2.60 (m, 2H), 2.26-2.30 (m, 6H), 1.93-1.96 (m, 1H).

mp 231-234° C.

Example 43

Compound (1-43)

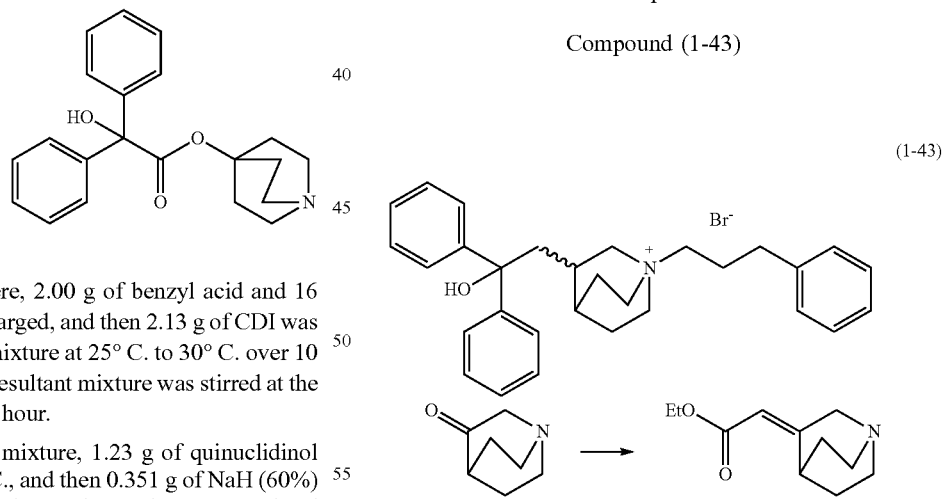

(1) Under an Ar atmosphere, 2.00 g of benzyl acid and 16 mL of dry DMF were charged, and then 2.13 g of CDI was dividedly added to the mixture at 25° C. to 30° C. over 10 minutes. After that, the resultant mixture was stirred at the same temperature for 1 hour.

Next, into the resultant mixture, 1.23 g of quinuclidinol was added at 5° C. to 10° C., and then 0.351 g of NaH (60%) was added to the mixture. The resultant mixture was stirred at 20° C. to 30° C. for 4 days.

The reaction mixture was cooled down to an internal temperature of 5° C. to 10° C., and was slowly added dropwise to 120 mL of water (white crystals precipitated). The mixture was aged and stirred at an internal temperature of 5° C. to 10° C. for around 6 hours, and then the precipitated crystals were collected by filtration, washed with 20 mL×3 of water, dried at 50° C. to 55° C. for 4 hours under reduced pressure, to give quinuclidinol benzilic acid ester as white crystals.

(1) Under an Ar atmosphere, 7.49 mL of diethylphosphonoacetic acid ethyl ester and 68 mL of dry tetrahydrofuran (THF) were charged, and then 1.5 g of NaH (60%) was added to the mixture at 8° C. to 15° C. The resultant mixture was stirred at the same temperature for 30 minutes.

Next, to the mixture, 17 mL of dry THE solution of 4.27 g of quinuclidine-3-one was added dropwise. The resultant mixture was stirred at room temperature for 3 hours, and then stirred at 50° C. to 55° C. overnight.

After confirming the disappearance of the starting materials by thin-layer chromatography (TLC), the reaction mixture was poured into 200 mL of ice water and 200 mL of ethyl acetate (EtOAc), and the resultant mixture was stirred for a while.

After the standing and the liquid separation, the obtained organic layer was washed successively with 200 mL of saline solution, and then the organic layer was dried over anhydrous magnesium sulfate and concentrated under reduced pressure to obtain concentrated residues.

The obtained concentrated residues were purified by silica gel column chromatography (120 g of NH silica gel, Heptane/EtOAc=9/1 to 1/1), to give 3-quinuclidylidene-acetic acid ethyl ester (6.43 g) as colorless oil.

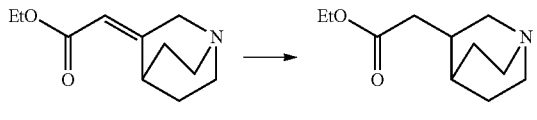 [SMILES: CCOC(=O)/C=C1/CN2CCC1CC2 ; CCOC(=O)CC1CN2CCC1CC2]

(2) The compound obtained in (1) in an amount of 6.00 g and 60 mL of EtOH were charged, and then 0.6 g of 10% Pd—C (50% wet) was added to the mixture. The resultant mixture was hydrogenated stirred overnight at normal pressure and room temperature under a $H_2$ atmosphere.

After confirming the disappearance of the starting materials by TLC, the Pd—C was filtered through Celite, and washed with EtOH, the filtrate was concentrated under reduced pressure, to give quinuclidine-3-acetic acid ethyl ester (6.05 g, yield 99.8%) as colorless oil.

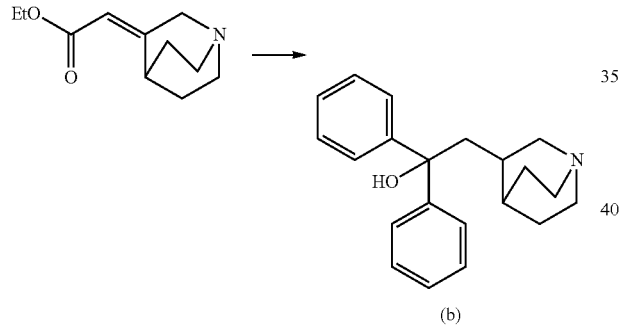

(b)

(3) Under an Ar atmosphere, 2.30 g of quinuclidine-3-acetic acid ethyl ester and 22 mL of dry THF were charged, and then 1.90 mL of 3M PhMgBr/THF solution was added dropwise to the mixture at 4° C. to 6° C. over 30 minutes. The resultant mixture was stirred at 50° C. to 55° C. for 4 hours.

After confirming the disappearance of the starting materials by TLC, the reaction mixture was ice-cooled, and into the cooled mixture, 20 mL of a saturated $NH_4Cl$ aqueous solution was slowly added dropwise, and the reaction was quenched.

The precipitated solid was collected by filtration, washed with $H_2O$, and dried under reduced pressure, to give 37.0 g of a treated crude product of the target object (37.0 g) as white crystals. The obtained product was purified by silica gel column chromatography (37 g of NH silica gel, $CHCl_3$/MeOH=10/1), and then the purified product was concentrated under reduced pressure to obtain fractions containing the target object.

The obtained residues were crystallized by MeOH-THF-IPE, to give the target object (b) (1.86 g) as white crystals.

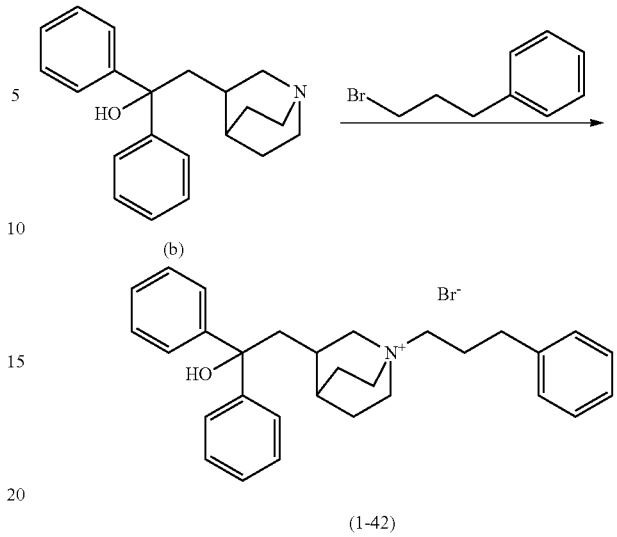

(1-42)

(4) Under an Ar atmosphere, 1.86 g of a compound (b) and 37 mL of dry acetone were charged, and then 1.84 mL of 3-phenylpropyl bromide was added to the mixture at 20° C. to 30° C. The resultant mixture was stirred at the same temperature for 4 days (90 h).

The reaction mixture was ice-cold stirred for 2 hours, and then the precipitated crystals were collected by filtration, washed with 40 mL×3 of IPE, and dried at 50° C. to 55° C. for 3 hours under reduced pressure, to give a treated crude product of a compound (1-42) (2.48 g) as white crystals. After dissolving 2.48 g of the crystals by MeCN—$H_2O$, the resultant mixture was crystallized by MeCN, to give the compound (1-42) (0.905 g) as white crystals.

$^1$H NMR (DMSO-$d_6$): δ=7.18-7.47 (m, 15H), 5.68 (s, 1H), 3.22-3.31 (m, 3H), 3.02-3.06 (m, 3H), 2.44-2.57 (m, 5H), 1.62-2.12 (m, 7H).

mp 194-197° C.

Example 44

Compound (1-44)

(1-44)

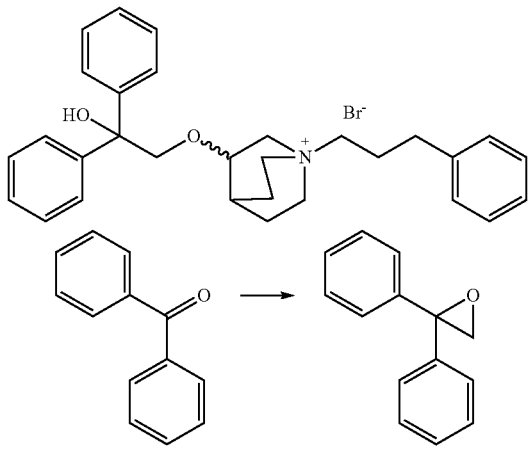

(1) Under an Ar atmosphere, 14.49 g of trimethylsulfonium iodide and 60 mL of dry dimethyl sulfoxide (DMSO) were charged, and then 2.63 g of NaH (60%) was dividedly added to the mixture at 20° C. to 30° C. The resultant mixture was stirred at the same temperature for 1.5 hours.

Next, to the mixture, 10.0 g of benzophenone was dividedly added, and the resultant mixture was stirred at 45° C. to 52° C. for 1 hour.

After confirming the disappearance of the starting materials by TLC, the reaction mixture was poured into 200 mL of ice water and 200 mL of EtOAc, and the resultant mixture was stirred for a while.

After the standing and the liquid separation, the obtained organic layer was washed successively with 200 mL of a saturated NaHCO$_3$ aqueous solution and 200 mL of saline solution, and then the organic layer was dried over anhydrous magnesium sulfate and concentrated under reduced pressure, to give concentrated residues (11.7 g).

The obtained concentrated residues were purified by silica gel column chromatography (120 g of silica gel, Heptane/EtOAc=60/1 to 40/1 to 20/1), and then the column fractions containing the target object was concentrated under reduced pressure, to give 1,1-diphenylethylene oxide (3.94 g, yield 36.6%) as colorless oil.

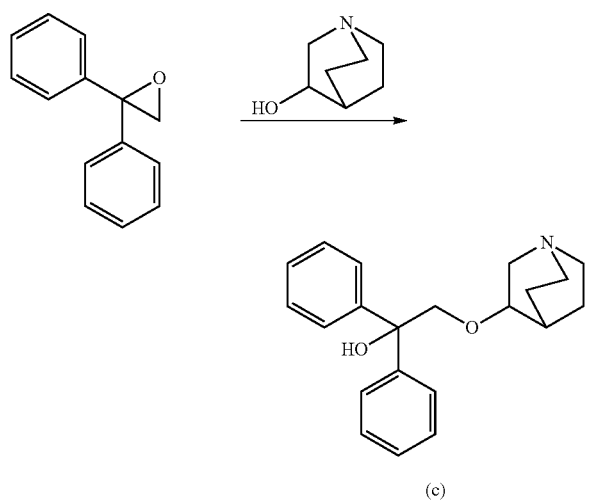

(c)

(2) Under an Ar atmosphere, 3.29 g of 3-quinuclidinol and 27 mL of dry DMF were charged, and then 1.03 g of NaOH (60%) was dividedly added to the mixture at 20° C. to 30° C. The resultant mixture was stirred at 45° C. to 50° C. for 1 hour.

Next, to the mixture, 12 mL of dry DMF solution of 3.90 g of 1,1-diphenylethylene oxide was added dropwise, and the resultant mixture was stirred at an internal temperature of 40° C. to 45° C. overnight.

After confirming the disappearance of the starting materials by TLC, the reaction mixture was ice-cooled, and into the cooled mixture, 160 mL of H$_2$O was slowly added dropwise (white crystals precipitated). The mixture was aged and stirred at an internal temperature of 5° C. to 10° C. for around 2 hours, and then the precipitated crystals were collected by filtration, washed with 20 mL×3 of H$_2$O, dried at 50° C. to 55° C. for 4 hours under reduced pressure, to give a treated crude product of the target object (c) (4.22 g) as a pale brownish white solid.

The obtained treated crude product in an amount of 4.22 g was recrystallized by THF-IPE to give the target object (a) (2.21 g) as white crystals.

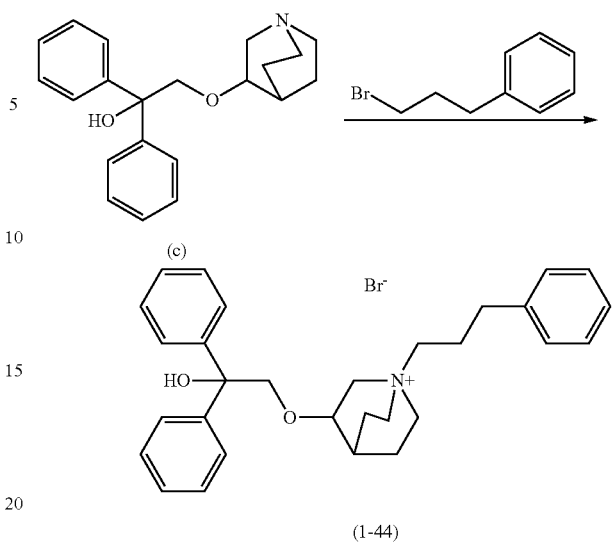

(1-44)

(3) Under an Ar atmosphere, 2.18 g of phenylpropyl bromide and 44 mL of dry acetone were charged, and then 2.05 mL of 3-phenylpropyl bromide was added to the mixture at 20° C. to 30° C. The resultant mixture was stirred at the same temperature for 3 days (65 h) (white suspension→white suspension).

The reaction mixture was ice-cold stirred for 2 hours, and then the precipitated crystals were collected by filtration, washed with 40 mL×2 of IPE, and dried at 50° C. to 55° C. for 3 hours under reduced pressure, to give a compound (1-44) (3.38 g) as white crystals.

$^1$H NMR (DMSO-d$_6$): δ=7.17-7.44 (m, 15H), 5.70 (s, 1H), 3.94-4.05 (m, 3H), 3.51-3.62 (m, 1H), 3.27-3.31 (m, 5H), 2.95-3.30 (m, 4H), 2.49-2.56 (m, 2H), 1.49-2.42 (m, 7H).

Test Example 2

Effect on Methacholine-induced Airway Constriction

<Method>

The increase of airway resistance by methacholine induction was measured. To 4 to 6-week old ICR mice, methacholine at 1 mg/mL was administered 5 times by spraying the methacholine for 20 seconds. After completion of the methacholine administration, the airway resistance was measured by a snap shot technique. All of the data were analyzed by using FlexiVent software.

The test compound at 47.9 µg/kg was administered to the mice through the transairway. The mice were exposed 5 times to nebulized methacholine 1 hour, 96 hours, and 120 hours after the administration, and the airway resistance at each time was measured.

Figure 2:
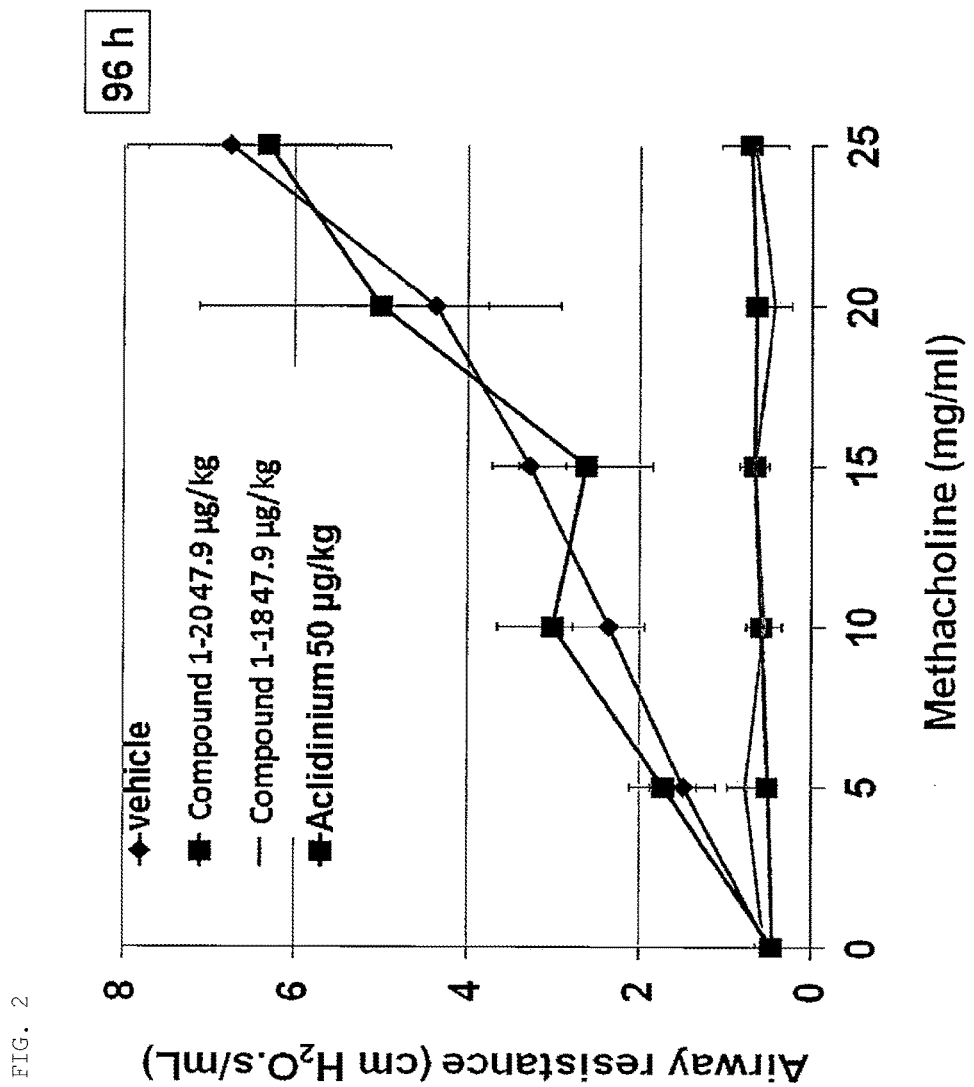
FIG. 2 shows effects of the compounds of the present invention and aclidinium (compound of Example 44 in Patent Literature 1) on methacholine-induced airway constriction (96 hours after administration).
Figure 3:
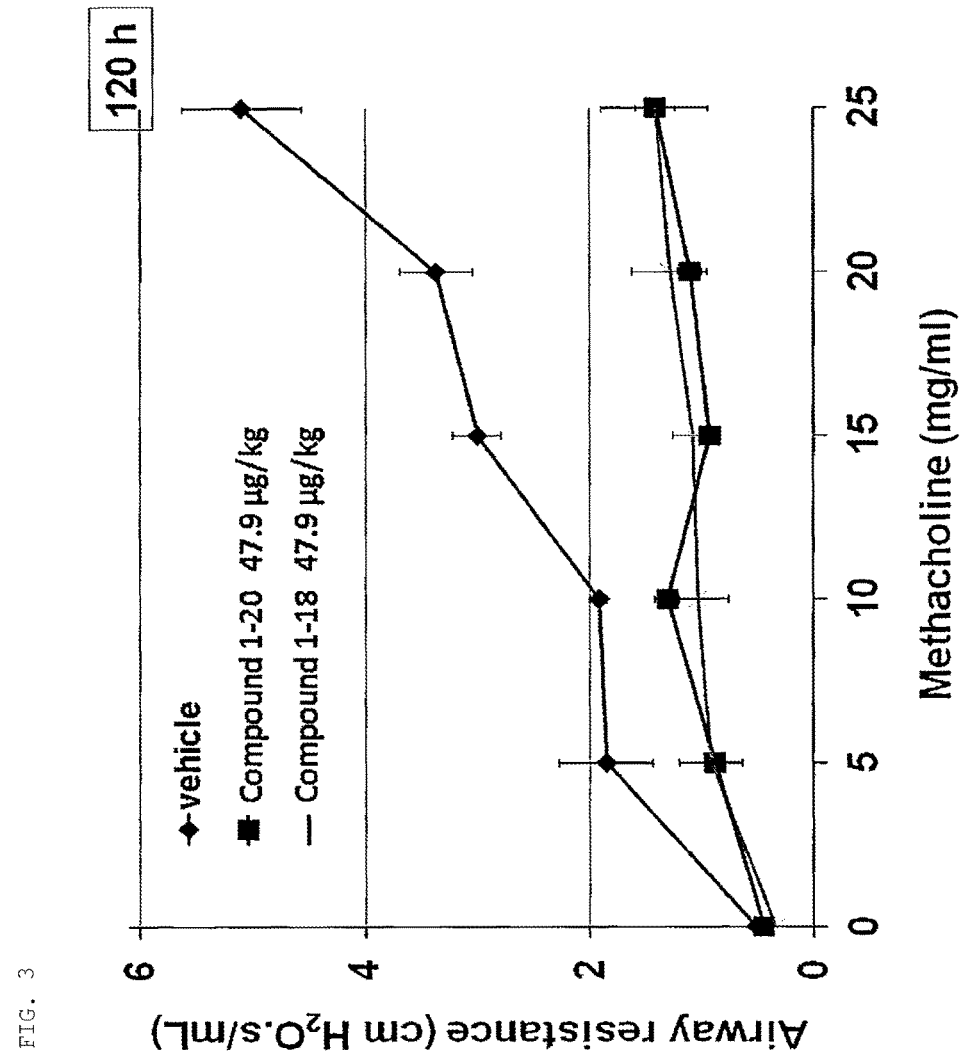
FIG. 3 shows effects of the compounds of the present invention on methacholine-induced airway constriction (120 hours after administration).

The results are shown in FIGS. 1 to 3.

<Results>

As can be seen from the results shown in FIGS. 1 to 3, the compound (1-18) and the compound (1-20) reduced the airway resistance at 47.9 µg/kg even 120 hours after the administration. In contrast, as shown in FIG. 2, aclidinium did not reduce the airway resistance when exceeding 96 hours after the administration.

Test Example 3

Effect on Porcine Pancreatic Elastase-induced Inflammation

<Method>

To 4 to 6-week old ICR mice, a test compound was administered once through the transairway. Porcine pancreatic elastase at 100 μg/mouse was administered 1 hour after the administration of the test compound. Bronchoalveolar lavage fluid (BALF) was collected from the lungs 24 hours after the administration of porcine pancreatic elastase, and the total number of cells was measured. The results are shown in FIG. 4.

<Results>

Figure 4:
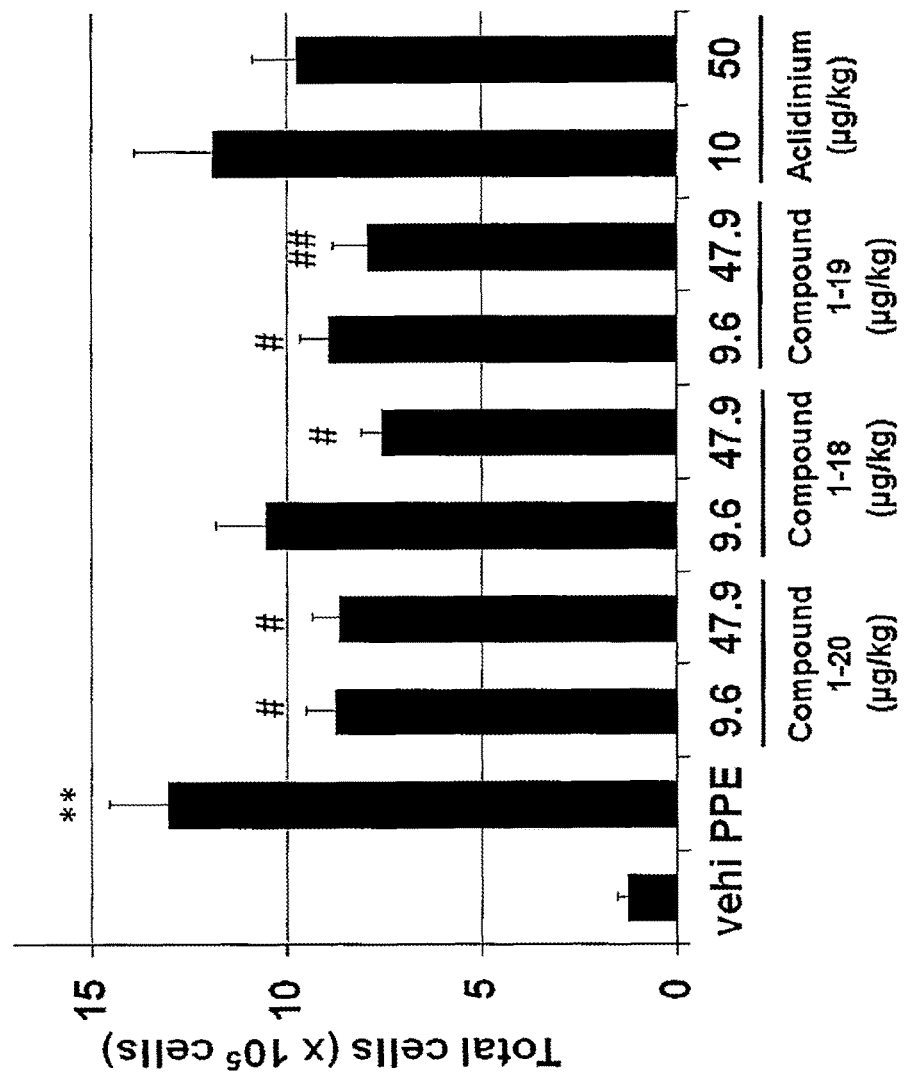
FIG. 4 shows anti-inflammatory effects of the compounds of the present invention and aclidinium.

As can be seen from the results shown in FIG. 4, the total number of cells in BALF was reduced in a dose-dependent manner of the compound (1-18), the compound (1-19), and the compound (1-20). In contrast, aclidinium did not show any beneficial anti-inflammatory effects.

From the results described above, it was found that the compounds of the present invention are effective against the inflammatory symptoms caused by porcine pancreatic elastase.

INDUSTRIAL APPLICABILITY

The compounds of the present invention have a long-term bronchodilation effect, and further show the efficacy against the inflammatory symptoms caused by pancreatic elastase of a porcine animal that is a COPD model, therefore, are extremely useful as a therapeutic agent for COPD having a bronchodilation effect and an anti-inflammatory effect at the same time.

The invention claimed is:

1. A quinuclidine derivative of the general formula (1):

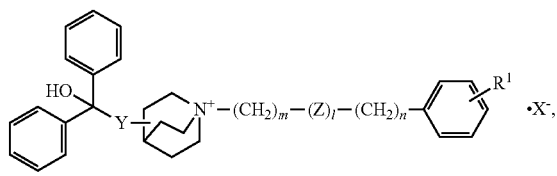

(1)

wherein:
R$^1$ represents a hydrogen atom, a halogen atom, a lower alkyl group, a haloalkyl group, a lower alkoxy group, or a haloalkoxy group;
Y is —C(=O)—O;
m is an integer of 1 to 5;
Z is an oxygen atom or a sulfur atom;
l is 0;
n is an integer of 0 to 4; and
X$^-$ is an anion;
substituents of a quinuclidine ring in the formula (1) are in a 1,3-position or 1,4-position.

2. The quinuclidine derivative according to claim 1, wherein:
m is an integer of 2 to 5; and
n is a number of 0 or 1.

3. The quinuclidine derivative according to claim 1, wherein n is 0.

4. The quinuclidine derivative according to claim 1, wherein
m is 3.

5. The quinuclidine derivative according to claim 1, wherein the quinuclidine derivative is an (R) isomer.

6. A pharmaceutical composition, comprising the quinuclidine derivative of claim 1, and a pharmaceutically acceptable carrier.

7. A method for treating chronic obstructive pulmonary disease, the method comprising administering an effective amount of the quinuclidine derivative according to claim 1.

8. The pharmaceutical composition of claim 6, wherein the pharmaceutical composition is in the form of an inhalant, a transairway agent, a nose drop, an injection, a tablet, a granule, a powder, a capsule, an ointment, a cream, a patch, a suppository, or a combination thereof.

9. The pharmaceutical composition of claim 6, wherein the quinuclidine derivative is included in an amount of at least 0.01% by mass based on the total amount of the composition.

10. The pharmaceutical composition of claim 6, wherein the quinuclidine derivative is included in an amount of at least 1% by mass based on the total amount of the composition.

11. The method of claim 7, wherein 1.0 μg to 10 mg of the quinuclidine derivative is administered per day.

12. The method of claim 7, wherein the quinuclidine derivative is administered via transnasal or transpulmonary administration.

13. The quinuclidine derivative of claim 1, wherein:
m is 3; and
n is 0.

14. A pharmaceutical composition, comprising the quinuclidine derivative of claim 2, and a pharmaceutically acceptable carrier.

15. A method for treating chronic obstructive pulmonary disease, the method comprising administering an effective amount of the quinuclidine derivative of claim 2.

16. The pharmaceutical composition of claim 14, wherein the pharmaceutical composition is in the form of an inhalant, a transairway agent, a nose drop, an injection, a tablet, a granule, a powder, a capsule, an ointment, a cream, a patch, a suppository, or a combination thereof.

17. A pharmaceutical composition, comprising the quinuclidine derivative of claim 3, and a pharmaceutically acceptable carrier.

18. A method for treating chronic obstructive pulmonary disease, the method comprising administering an effective amount of the quinuclidine derivative of claim 3.

19. The pharmaceutical composition of claim 17, wherein the pharmaceutical composition is in the form of an inhalant, a transairway agent, a nose drop, an injection, a tablet, a granule, a powder, a capsule, an ointment, a cream, a patch, a suppository, or a combination thereof.

* * * * *

UNITED STATES PATENT AND TRADEMARK OFFICE
CERTIFICATE OF CORRECTION

PATENT NO. : 10,155,755 B2
APPLICATION NO. : 15/552623
DATED : December 18, 2018
INVENTOR(S) : Tohru Mizushima et al.

It is certified that error appears in the above-identified patent and that said Letters Patent is hereby corrected as shown below:

In the Claims

Column 29, Line 52, "Y is -C(=O)-O;" should read -- Y is -C(=O)-O-; --.

Signed and Sealed this
Twenty-seventh Day of August, 2019

Andrei Iancu
*Director of the United States Patent and Trademark Office*